United States Patent [19]

Shug et al.

[11] Patent Number: 5,569,457
[45] Date of Patent: Oct. 29, 1996

[54] METHOD OF STIMULATING ANTIBODY FORMATION

[76] Inventors: Austin L. Shug, 5322 Lighthouse Bay Dr., Madison, Wis. 53704; Stefan Gravenstein, 710 N. Meadow La., Madison, Wis. 53705

[21] Appl. No.: 341,758

[22] Filed: Nov. 18, 1994

[51] Int. Cl.$^6$ ............... A61K 31/205; A61K 39/145
[52] U.S. Cl. ................ 424/278.1; 424/209.1
[58] Field of Search ................ 424/278.1, 209.1

[56] References Cited

U.S. PATENT DOCUMENTS

| | | | |
|---|---|---|---|
| 4,382,092 | 5/1983 | Cavazza | 514/556 |
| 4,415,588 | 11/1983 | Cavazza | 514/547 |
| 4,812,478 | 3/1989 | Tinti et al. | 514/550 |
| 5,030,458 | 7/1991 | Shug et al. | 426/2 |

FOREIGN PATENT DOCUMENTS

| | | |
|---|---|---|
| WO 89/10065 | 11/1989 | WIPO . |
| WO 91/07880 | 6/1991 | WIPO . |

OTHER PUBLICATIONS

C. Franceschi et al., *Int. J. Clin. Pharm.*, Res. X (1/2) pp. 53–57 (1990).
*Nutr. Rev.*, vol. 36 (1978) pp. 305–309 (no author).
F.C.M. Chen et al., *Can. J. Chem.* vol. 54 (1976) pp. 3310–3311.
P. G. Welling et al., *Int. J. Clin. Pharm. Biopharm.*, vol. 17 (1979) pp. 56–60.
M. L. Schinetti et al., *Int. J. Tiss. Reac.* VIII(3) pp. 199–203 (1986).
J. C. Cambier et al., *The FASEB Journal*, vol. 6 (Oct. 1992) pp. 3207–3217.
C. J. Rebouche et al., *May Clin. Proc.*, vol. 58, pp. 533–540 (1983).
A. Marzo et al., *Eur. J. Clin. Pharmacol.*, vol. 37, pp. 59–63 (1989).
P. Lefresne et al., *Biochimie*, vol. 59, pp. 197–215 (1977).
M. Onofrj et al., *Drugs Exptl. Clin.*, Res. IX(2), pp. 161–169 (1983).
A. Shug et al., *Cardiovascular Drugs and Therapy*, vol. 5, pp. 77–84 (1991).
S. V. Pande et al., *Analytical Biochemistry*, vol. 112, pp. 30–38 (1981).
P. R. Borum, *Can. J. Physiol. Pharmacol.*, vol. 63, pp. 571–576 (1985).
Believed to be J. Bremer, *Trend in Biochemical Sciences*, vol. 2, pp. 31–33 (1977).
S. C. Winter et al., *American Journal of Diseases of Children*, vol. 141, pp. 660–665 (1987).

*Primary Examiner*—Mindy Fleisher
*Assistant Examiner*—Terry A. McKelvey
*Attorney, Agent, or Firm*—Grady J. Frenchick; Stroud, Stroud, Willink, Thompson & Howard

[57] ABSTRACT

A method and composition for the enhanced stimulation of antigenic response in animals and humans is disclosed. The method involves administering an effective amount of a compound of formula (I):

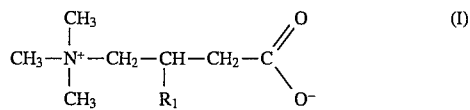

wherein $R_1$ is hydrogen or hydroxyl. L-carnitine and gamma-butyrobetaine are preferred compositions embraced by formula (I).

16 Claims, 5 Drawing Sheets

FIG. 1

Adjusted mean antibody response to Beijing hemagglutinin measured in optical density at 410 nm. *=p-value of control versus supplemented.

FIG. 2

Adjusted mean antibody response to Panama hemagglutinin measured in optical density at 410 nm. *=p-value of control versus supplemented.

FIG. 3

Adjusted mean antibody response to Taiwan hemagglutinin measured in optical density at 410 nm. *=p-value of control versus supplemented.

METHOD OF STIMULATING ANTIBODY FORMATION

TECHNICAL FIELD

The invention relates generally to the fields of immunology and preventive medicine, and in particular to the use of adjuvants or other substances to enhance immune responsiveness to vaccinations in animals or humans with compromised immune systems. Specifically, the invention is directed to use of L-carnitine and/or its precursors with vaccines to effectively stimulate an improved antigenic response.

BACKGROUND OF THE INVENTION

In middle and late adulthood, all people experience a series of progressive alterations in body physiology and composition. One physiological change associated with aging is immune system senescence. This senescence is characterized by a decline in both B-cell (humoral) and T-cell (cellular) immune responses. B-cells and T-cells are collectively known as lymphocytes. In basic terms, the B-cell immune response is responsible for the production of specific antibodies targeted to specific antigens such as bacteria and viruses. The T-cell immune response is responsible for the production of activated T-cells which recognize and destroy foreign tissues and cells infected with pathogens. It also produces lymphokine secreting helper T-cells that stimulate the bodies overall immune response.

The decline in the immune response with age is thought to be a major contributor to the relatively higher susceptibility of elderly people to infectious diseases and to cancer. Of the infectious diseases, influenza infection is a major health problem causing death in a significant percentage of elderly people contracting the disease each year. The institution of vaccination programs to protect the elderly from influenza have been only partially successful, mainly because the elderly are significantly less likely to develop a protective antibody response to the influenza vaccines than younger people. Thus, the development of a safe, effective and convenient method for enhancing the efficacy of vaccines would be an important step forward in the field, particularly influenza vaccines, of preventive medicine.

Another physiologic change associated with aging is the decreased oxidation of fatty acids. This metabolic process, which is a major source of cellular energy, takes place in the mitochondria. Before most fatty acids can be metabolized, however, they must be esterified with L-carnitine to form acylcarnitine. The fatty acid acylcarnitine can then be transported across the mitochondrial membrane. Once inside the mitochondria, the acyl group is transferred to Coenzyme A. The carnitine is then transported back out of the mitochondria either in its free form or is esterified to acyl groups needed to be removed from the organelle. Thus, carnitine has two critical functions in the cell, namely, (1) to stimulate fatty acid oxidation by transporting acyl groups across the inner mitochondrial membrane, resulting in adenosine triphosphate (ATP) formation, and (2) to remove extra or "toxic" acyl groups from the mitochondria and cell as carnitine esters.

L-carnitine is present in serum and urine in both free and esterified forms. In humans, normal total serum carnitine concentrations range from about 25–79 µM, and free carnitine concentrations range from about 21–68 µM. One indication of the level of fatty acid oxidation in an individual is the ratio of acylcarnitine (esterified carnitine) to free L-carnitine in these fluids, referred to as the E/F ratio. An E/F ratio greater than 0.25 is indicative of reduced oxidative activity; therefore, it is not surprising that 65% of adults over the age of 65 have an E/F ratio exceeding 0.25 since, as mentioned above, fatty acid oxidation tends to be reduced in this population of people.

In addition to its role in the oxidation of fatty acids, L-carnitine has also been found to exhibit some immunomodulatory effects in vitro. For example, Franceschi C. et al. showed that phytohaemagglutinin-induced peripheral blood lymphocyte proliferation was markedly increased by acetyl-L-carnitine-preloaded lymphocytes from young and especially old subjects. *Int. J. Clin. Pharm.*, Res. X (½) 53–57 (1990). In addition, U.S. Pat. No. 4,415,588, issued to Cavazza, discloses that the incubation of mouse and human lymphocytes with L-acetylcarnitine and phytohemagglutinin or concanavalin A in vitro, resulted in a larger proliferative response than that seen if the mitogens were used alone.

These reports, while important observations, leave many questions unanswered. For example, they are all in vitro studies and, therefore, it is unknown whether their effects in vitro would also occur in vivo. Also, there was no characterization of which population of lymphocytes, the B-cells or T-cells, were proliferating in response to the effectors.

Vaccines function by introducing antigens into the body which can then bind to the surface antibodies of circulating B-cells. The binding of the antigen to the B-cell surface antibody activates the B-cell causing it to proliferate and synthesize and secrete antigen-specific antibodies. Mitogens can also cause B-cells to proliferate, however, unlike the proliferation generated by an antigen-antibody interaction, the proliferation of B-cells caused by mitogens is independent of their ability to produce antibodies. Unless a B-cell is already activated to produce a specific antibody, a proliferative response generated by a mitogen will not result in increased production of specific antibodies by the cell. Further, even if a B-cell is already activated, the mitogen induced proliferation may or may not stimulate greater antibody production by the cells.

For an immunomodulator to be of use as an adjuvant, it would have to increase the antigenicity of the vaccine, increase the production of antigen-specific antibodies by activated B-cells, and/or increase the rate of proliferation of the activated B-cells.

Some of the most potent adjuvants presently known cannot be used in clinical practice because they are either toxic or cause potentially fatal hypersensitivity reactions in animals after several exposures. These include Freund's adjuvant, incomplete Freund's adjuvant, and keyhole limpet hemocyanin.

Other adjuvants with either potential or proven clinical application fall into two categories; those that are delivered with the vaccine antigen as part of the injection, and those that are administered separately.

Those adjuvants falling within the first category include alum, gram negative bacterial derivatives, mycobacterial derivatives, and lipid derivatives. Alum has no serious side effects but is considered a very weak adjuvant. The gram negative bacterial derivatives, including monophosphorylated derivative A (MPL), Bacille Calmette-Guerin (BCG), and lipopolysaccharide (LPS) are potent adjuvants. However, they may uncouple T-cell regulation of B-cells and there is currently concern that they may, therefore, have carcinogenic potential. The mycobacterial derivatives such as trehalose dimycolate (TDM) and cell wall cytoskeleton (CWS) have been used successfully as adjuvants only in conjunction with MPL. Therefore, the above concerns regarding the use of MPL also apply to these compounds. The lipid derivatives are the carriers used to deliver other adjuvants which also have weak immunostimulatory properties on their own; squalene is one example.

Adjuvants that are administered separately from the vaccine injection include thymic hormone derivatives, dehydroepiandrosterone (DHEA) and melatonin. The thymic hormone derivatives such as thymosin alpha 1 and thymulin have only mild immunostimulatory effects. They also suffer the disadvantage of being impractical since several injections are required to elicit the desired response.

The use of DHEA and melatonin as adjuvants is new and as yet poorly studied. Both compounds naturally decline with age (as do the thymic hormones), can be administered orally, and appear to be nontoxic. Their effectiveness as adjuvants, however, remains to be determined.

It is clear from this array of information that to date an adjuvant has not been developed that combines the advantages of a high degree of potency, convenience of administration, and the absence of any health risk. Thus, the prior art teaches age-linked diminished immune response and age-linked decrease in oxidative metabolism of fatty acids. The prior art also teaches the use of carnitine to enhance the proliferative response of lymphocytes in vitro. The art does not, however, provide any link between the in vivo administration of L-carnitine to animals (or humans) and enhanced production of antibodies by B-cells in response to concomitant vaccine administration.

SUMMARY OF THE INVENTION

The present invention provides a method for improving the efficacy of vaccines through concomitant treatment or administration of animals or humans at the time of vaccination with L-carnitine and its precursors thereof as defined in formula (I):

wherein $R_1$ is selected from the group consisting of hydrogen (—H) or hydroxyl (—OH). With the exception of the data provided herein, no clinical data are available which correlates treatment of animals or humans with L-carnitine or its precursors with improved antibody production in response to vaccination.

It has now been found unexpectedly that the concomitant use of compounds of formula (I) and vaccines can increase the immune responsiveness of animals resulting in higher serum antibody levels specific to the vaccine antigen three to four weeks post-vaccination. As explained in detail hereinbelow, Balb/c mice administered influenza or pneumococcal vaccines showed higher levels of antibodies specific to the vaccine antigens as compared to the levels of antibodies produced by paired groups of control mice fed a diet not supplemented with L-carnitine. This ability of compounds of formula (I) to increase the levels of antibodies produced in response to antigen stimulation occurred in both young and old animals. However, the increases in antibodies seen were substantially greater in the older animals. Thus, the present invention provides novel methods and compositions for increasing the efficacy of vaccines, particularly in animals with compromised immune response systems. A specific illustrative example of animals with compromised immune response systems, as the term is used herein, is aged animals.

The foregoing, and other advantages of the present invention, are realized in one aspect thereof in a method for increasing the levels of antibodies produced in response to vaccine administration by treating animals for several weeks starting around the day of innoculation with the antigen (e.g., by injection) with an effective amount of a compound of formula (I). Animals are treated with compounds of formula (I) in a daily oral dose of about 5 mg/kg body weight to about 500 mg/kg body weight, preferably about 10 mg/kg body weight to about 100 mg/kg body weight. Administration of a compound of formula (I) continues generally on a daily basis throughout the time period of antibody generation. This time period can be as short as one week to as long as six months or more. Preferably, a formula (I) compound is administered daily, for a period of about two months to about five months after antigen administration.

The terms "treating" or "administering" are to be broadly construed to obtain the advantages of this invention. Specifically, "administering" can mean, e.g., oral administration or administration by injection (e.g., intramuscular injection). Also, "administering" of a compound of formula (I) as intended herein may be simulataneous with vaccine administration, and may be before or after vaccine administration assuming it to be reasonably contemporaneous therewith. Also, formula (I) administration may be in single or preferably multiple proportionate doses and may be mixed with the selected antigen. Lastly, this invention is intended to relate to both human and animal antibody formations. If injected, a dosage quantity will fall in the range of 3 mg to 300 mg.

The compound of formula (I) is provided in pharmaceutical compositions in combination with a physiologically acceptable vehicle (when administered by injection) or in dietary compositions administered orally. These compositions constitute another aspect of the invention. Preferred in the compositions are compounds of formula (I) which include L-carnitine and gamma-butyrobetaine (a carnitine precursor as explained hereinbelow) or a combination of the foregoing.

Other advantages and a fuller appreciation of the specific adaptation, compositional variations and physical attributes of this invention will be gained upon an examination of the detailed description of preferred embodiments, taken in conjunction with the appended drawings and claims.

BRIEF DESCRIPTION OF THE DRAWINGS

The preferred exemplary embodiment of the present invention will hereinafter be described in conjunction with the appended drawings wherein like designations refer to like elements throughout and in which.

DETAILED DESCRIPTION

The present invention relates broadly to methods for improving the efficacy of vaccines, and specifically to a method for increasing the amount of antibody produced in response to vaccine administration by concomitant treatment of vaccinated animals (or humans) with compounds of formula (I) as defined hereinbelow, namely L-carnitine and gamma-butyrobetaine.

The present invention is intended for use in all animals having reduced immune responsiveness to antigenic stimulation, and therefore, relatively low antibody levels despite vaccine administration.

As used herein, the term "old" and "aged" is meant to designate in mice those which are at least 18 months old and the term "young" is meant to designate in mice those which are less than 5 months old. As used herein and generally in the art, the term "inner salt" refers to the fact that a molecule possess both a positive and negative charge, i.e., one part of the molecule functions as a cation while another part of the molecule acts as an anion. As used herein, the term "fourfold response" means an animal that had at least four times more antibody in their post-vaccination serum sample than in their pre-vaccination serum sample.

In one of its aspects, the invention is a method for enhancing the production of antibodies in response to vaccine administration comprising treating an animal at the time of vaccination with an effective amount of a compound of formula (I):

wherein $R_1$ is selected from the group consisting of hydrogen or hydroxyl. While the compounds of formula (I) are illustrated as inner salts, alternative forms such as the protonated carboxylate group, that is, e.g., a hydrochloride, are considered within the scope of the present invention. When $R_1$ is hydrogen, the compound is 4-trimethylamino butyrate, also known as γ-butyrobetaine; when $R_1$ is hydroxyl, the compound is L-carnitine. Preferred embodiments include γ-butyrobetaine, L-carnitine or a combination thereof. The "effective amount," as the term is used herein, is suitably an amount effective to increase the quantity of antibodies produced in response to vaccine administration above that attained if a compound of formula (I) is not given. As an example, the amount of compound of formula (I) sufficient to produce a 10% increase in antibody formation versus antibody formation in the absence of a compound of formula (I) is "an effective amount."

It is noted that γ-butyrobetaine is the precursor of L-carnitine in the biosynthetic pathway of the latter compound (*Nutr. Rev.*, vol. 36 (1978) pp. 305–309) and has been described as useful in certain carnitine deficiency states. U.S. Pat. No. 5,030,458 describes use of γ-butyrobetaine as a prophylactic agent for diet-induced carnitine deficiency in dogs and cats. U.S. Pat. No. 4,382,092 to Cavazza discloses use of γ-butyrobetaine to alleviate carnitine deficiency syndromes in humans beings. It is stressed, however, that the present invention is not directed toward carnitine deficiency, as that term is normally defined but, in one aspect, is directed toward patients with low normal plasma carnitine levels.

The compounds of formula (I) have been found to possess valuable biological activity, acting as effective adjuvants to vaccine administration. An "adjuvant", as the term is used herein, is any material which increases the immune response, e.g., the enhanced generation of antibodies. The compounds of formula (I) are water soluble, permitting ease of use by all means of drug delivery systems. The inner salt embodiment of formula (I) is particularly advantageous as it is readily soluble in water and dissolution provides a neutral solution of virtually physiologic pH. The compounds are commercially available from, e.g., Sigma Tau Chemical Co., Rome, Italy; Sigma-Aldrich Chemical Co., St. Louis, Mo. A method of preparing γ-butyrobetaine is described in *Can. J. Chem.* vol. 54 (1976) pp. 3310–3311 which description is incorporated by reference herein.

The compounds of formula (I) have very low toxicity, which enhances their pharmaceutical properties. Compounds of formula (I) have a toxicity, as measured by the $LD_{50}$ test, which is about twice that of sodium chloride, i.e., they are half as toxic as ordinary table salt.

The compounds of formula (I) are useful as active compounds in pharmaceutical compositions having reduced side effects and low toxicity. Such compositions may include physiologically acceptable vehicles or carriers. These pharmaceutical compositions constitute another aspect of the invention.

The pharmacologically active compounds of this invention can be processed in accordance with conventional methods of pharmacy to produce medicinal agents for administration to patients, e.g., mammals including human beings. For example, the compounds of formula (I), can be employed in admixtures with conventional excipients, e.g., pharmaceutically acceptable carriers suitable for enteral (e.g., oral), parenteral, or topical application which do not deleteriously react with the active compounds.

Suitable pharmaceutically acceptable carriers include, but are not limited to, water, salt solutions, alcohols, gum arabic, vegetable oils (e.g., corn oil, cottonseed oil, peanut oil, olive oil, coconut oil), fish liver oils, oily esters such as Polysorbate 80, polyethylene glycols, gelatine, carbohydrates (e.g., lactose, amylose or starch), foods, magnesium stearate, talc, silicic acid, viscous paraffin, fatty acid monoglycerides and diglycerides, pentaerythritol fatty acid esters, hydroxy methylcellulose, polyvinyl pyrrolidone, etc.

For enteral application, particularly suitable are tablets, dragees, drops, lozenges, powders, suppositories or capsules with, e.g., talc or a hydrocarbon excipient or binder such as lactose, cornstarch or potato starch. Use can also be in liquid form, e.g., as syrup, elixir, or the like to which a sweetener is added, if desired.

The pharmaceutical preparations can be sterilized and, if desired, can be mixed with auxiliary agents, e.g., lubricants, preservatives, stabilizers, wetting agents, emulsifiers, salts for influencing osmotic pressure, buffers, coloring and flavoring.

Oral administration of the pharmaceutical compositions of the present invention comprising the compounds of the present invention is preferred. The daily dosage of the compounds of formula (I) in accordance with the invention generally is about 5 to about 500 mg/kg animal body weight, preferably about 10 to 100 mg/kg animal body weight, orally.

It will be appreciated that the actual preferred amounts of active compound in a specific case will vary according to the efficacy of the specific compound employed, the particular compositions formulated, the mode of application, and the particular animal being treated. For example, the specific dose for a particular animal depends on age, body weight, general state of health, sex, on the diet, on the timing and mode of administration, on the rate of excretion, on medicaments used in combination, and on the severity of the impairment of the immune response. Dosages for a given host can be determined using conventional considerations, e.g., by customary comparison of the differential activities of the subject compounds and of a known agent, such as by means of an appropriate conventional pharmacological protocol.

The compounds in accordance with the present invention can also be used in humans. The daily dosage of the compounds of formula (I) is about 1 g to about 5 g, preferably about 2 g to about 4 g orally. Because the serum half-life of carnitine in human beings is about 30 minutes (P. G. Welling et al., *Int. J. Clin. Pharm. Biopharm.*, vol. 17 (1979) pp. 56–60), it is preferred that the daily dosage be divided into separate unit dosages to be administered separately, e.g., four separate unit dosages which are separately administered four times daily.

The present invention is further explained by the following examples which should not be construed by way of limiting the scope of the present invention. In the following examples, all mice used in the animal studies were female BALB/c strain obtained from Charles River Laboratories, National Institute on Aging, Bethesda, Md.

EXAMPLE 1: Effect of L-carnitine treatment of Balb/c mice on antibody levels attained 3 weeks after administration of the A/Taiwan/H1N1 vaccine.

Forty mice aged 17 months (i.e., "old" mice) were housed in separate microisolation cages. Prior to initiating the experiment the mice were acclimated for a period of seven days. The mice were then divided into two equal groups of 20 animals each, a control and an experimental group. The control group was fed a diet of Purina 5001 Rodent Chow (Teklad Premier, Madison, Wis.) that had been ground and then repelleted. Starting on the day of vaccination, the experimental group was fed a diet of Purina 5001 Rodent Chow to which 640 mg L-carnitine/Kg of chow had been added before repelleting. It was estimated that the consumption of this diet would result in the ingestion of 50 mg/Kg body weight/day of L-carnitine by the mice in the experimental group. All mice were provided with 35 grams of chow weekly. On the day of vaccination, all forty mice were injected intraperitoneally with 5.0 µg of the A/Taiwan/H1N1 influenza subunit vaccine. At the time of vaccination, a blood sample was taken from their retro-orbital plexus using heparinized micropipettes for determination of "pre-sera" antibody levels. The mice were similarly bled three weeks later for determination of "post-sera" antibody levels. The blood samples were separated by centrifugation in a refrigerated microfuge for 10 min. The serum was then removed and stored at −20° C. until assayed. Due to several factors, the post vaccination serum samples were incomplete for three of the mice in the experimental group. Therefore, in the final analysis, n=20 for the control group and n=17 for the experimental group.

On completion of the experiment, the pre- and post-sera samples were assayed for A/Taiwan/H1N1 antibody levels by ELISA. This assay involved a four day procedure as follows. On day 1, individual wells of Immunolon II microtiter plates (Dynatech; Chantilly, Va.) were each coated with 300 µl of a 0.03 µg/ml solution of A/Taiwan/H1N1 antigen contained in a 0.03 µg/ml Sodium Bicarbonate buffer, the plates were then incubated overnight at 4° C. On day 2, the wells were washed three times with pH 7.0 phosphate buffered saline to which 5% Tween-20 had been added (PBS-T), then 175 µl of 1:4000 dilutions (in PBS-T) of serum from the test mice were plated per well in quadruplicate. As controls, standards from pooled sera were also plated and several wells were plated without serum. The plates were incubated overnight at 4° C. On day 3, wells were washed three times with PBS-T after which 200 µl of a 1:5000 dilution in PBS-T of goat anti-mouse IgG F'(Ab)$^2$ conjugated to alkaline phosphatase (TAGO, Burlingame, Calif.) was added to each well. The plates were incubated overnight at 4° C. On day 4, wells were washed three times with PBS-T, 175 µl of 1 mg/ml paranitrophenol phosphate in 1M diethanolamine, pH 9.8 was added to each well. After 10 minutes the reaction was stopped by addition of 10 µl of 1M NaOH and optical densities were measured at 410 nm using a Dynatech 650 plate reader (Dynatech; Chantilly, Va.). (Optical density is a measure of antibody level.) A pooled serum sample was used as the reference standard. Optical densities of various amounts of the standard sample were plotted on semi-log paper to provide the basis for interpreting the optical densities of the experimental samples and to normalize optical densities between ELISA plates. The optical densities for quadruplicate determinations of the experimental samples were compared and assays were repeated when the standard error of the mean (s.e.m.) exceeded 0.10 optical density units.

Figure 1:
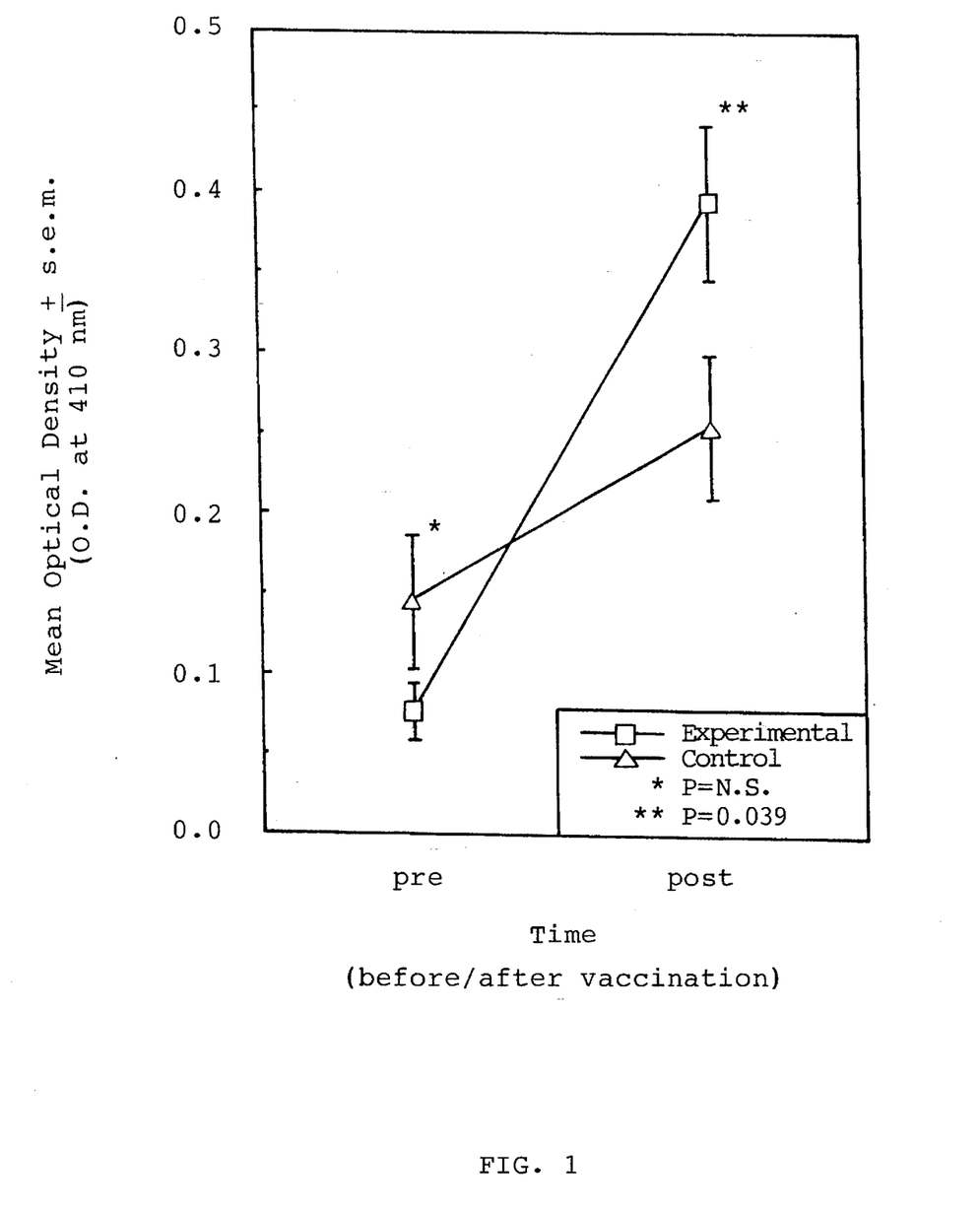
FIG. 1 is a graph of the mean optical densities obtained from sera of control and L-carnitine treated Balb/c mice before and 3 weeks after administration of the A/Taiwan/H1N1 vaccine.

FIG. 1 plots the mean optical densities (at 410 nm) obtained from the pre- and post-sera samples of both the control (no treatment) and experimental (L-carnitine treated) animals. Analysis of this data shows that the animals that received the L-carnitine supplemented diet had a 38% (p=0.039) greater antibody response than the animals receiving no supplementation. Further, only 10% of the control animals achieved a fourfold antibody response compared to 59% of the L-carnitine treated animals. This indicates that treatment of older (and therefore, presumably, less immunocompetent), animals with L-carnitine at the time of vaccination appears to augment the immune system responsiveness to the A/Taiwan/H1N1 antigen.

EXAMPLE 2: Effect of L-carnitine treatment of young and old Balb/c mice on antibody levels attained 3 weeks after administration of three influenza vaccines.

Mice were purchased as indicated above at either 2 months of age ("young") or 20 months in age ("old"). The two age groups of mice were divided into three subgroups, each subgroup receiving either the A/Beijing/H3N2, B/Panama/45, or A/Taiwan/H1N1 influenza vaccine. These subgroups were then further divided such that, as in Example 1, some received Purina 5001 rodent chow supplemented with L-carnitine (experimental) and some were fed unsupplemented chow (control). The number of animals falling into each group was as follows: young mice administered the A/Beijing/H3N2 vaccine, 19 experimental/20 control; young mice administered the B/Panama/45 vaccine, 19 experimental/20 control; young mice administered the A/Taiwan/H1N1 vaccine, 18 experimental/20 control; old mice administered the A/Beijing/H3N2 vaccine, 17 experimental/20 control; old mice administered the B/Panama/45 vaccine, 17 experimental/20 control; and old mice administered the A/Taiwan/H1N1 vaccine, 17 experimental/20 control. Collection of serum samples, antibody assay, and data analysis was performed as indicated in Example 1.

Figure 2:
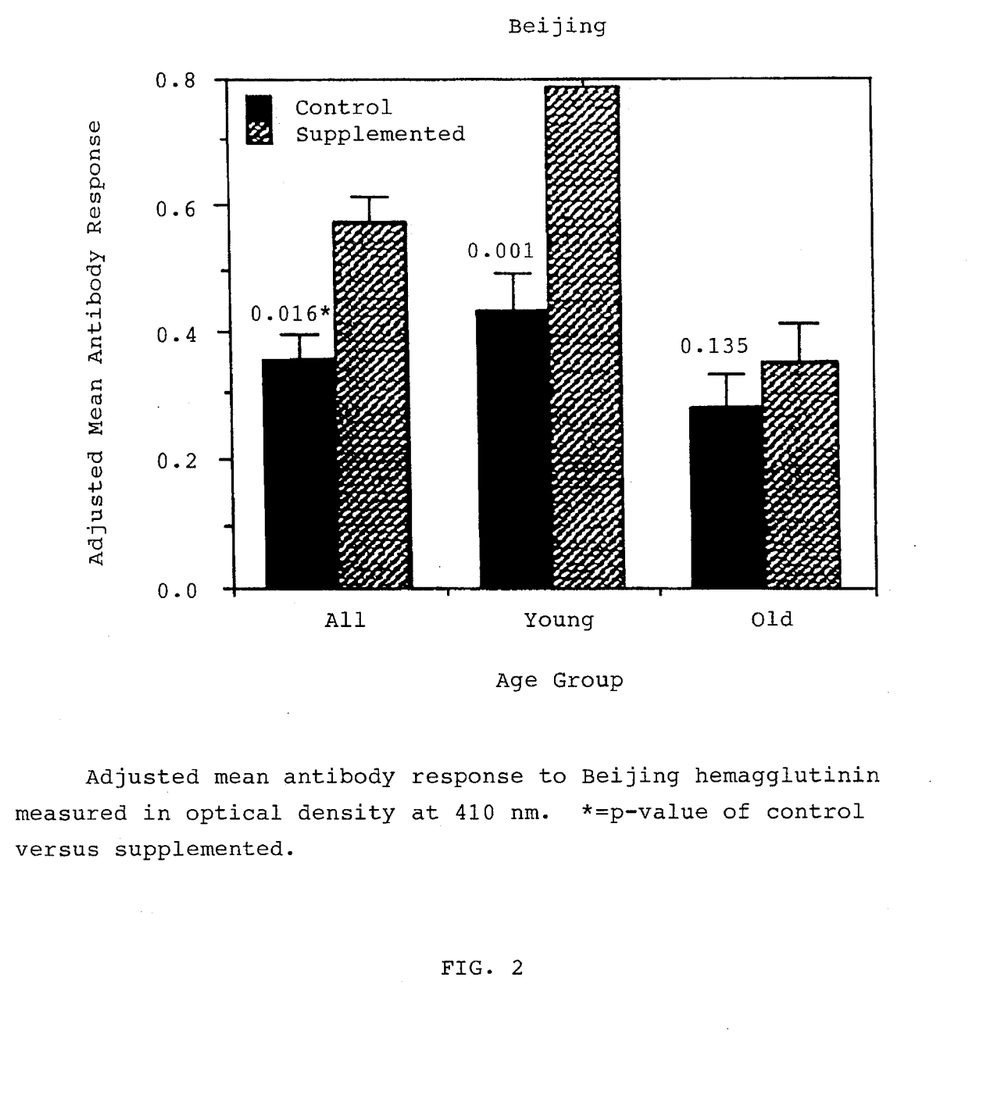
FIGS. 2, 3, and 4 are histograms of the mean optical densities obtained from sera of control and L-carnitine treated Balb/c mice 3 weeks, respectively, after administration of the A/Beijing/H3N2 vaccine, B/Panama/45 vaccine, or A/Taiwan/H1N1 vaccine.
Figure 3:
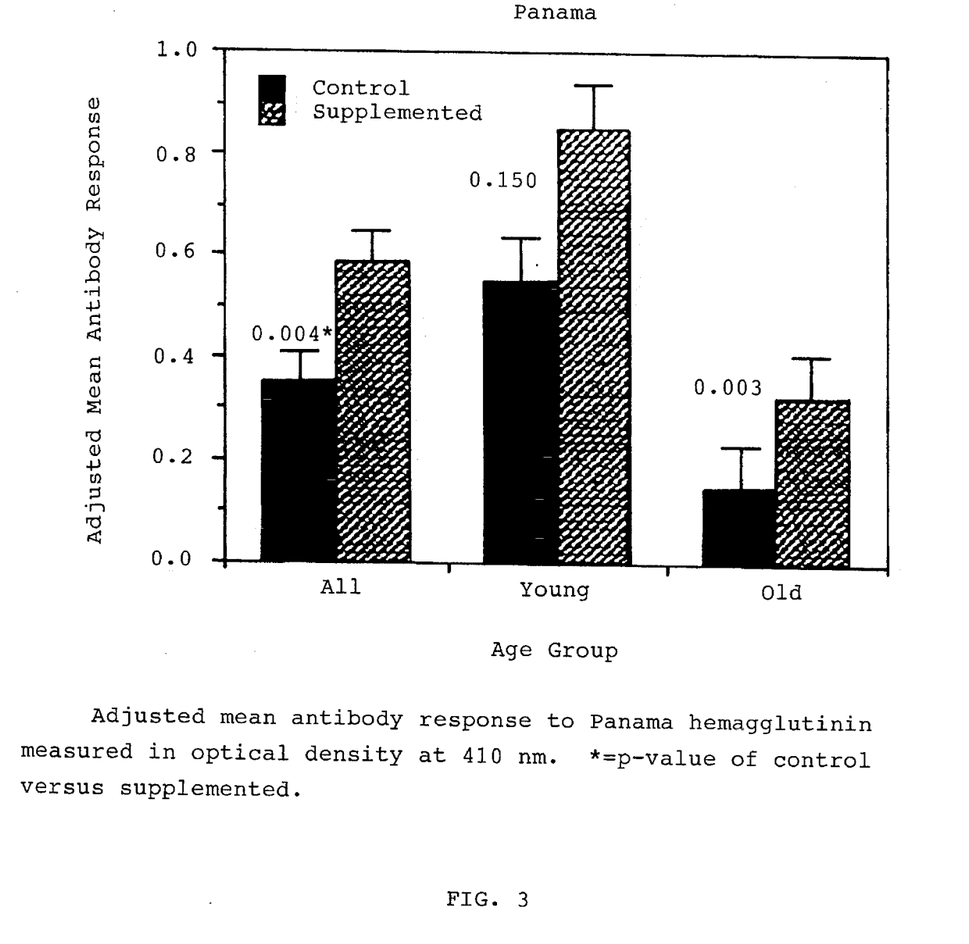
Figure 4:
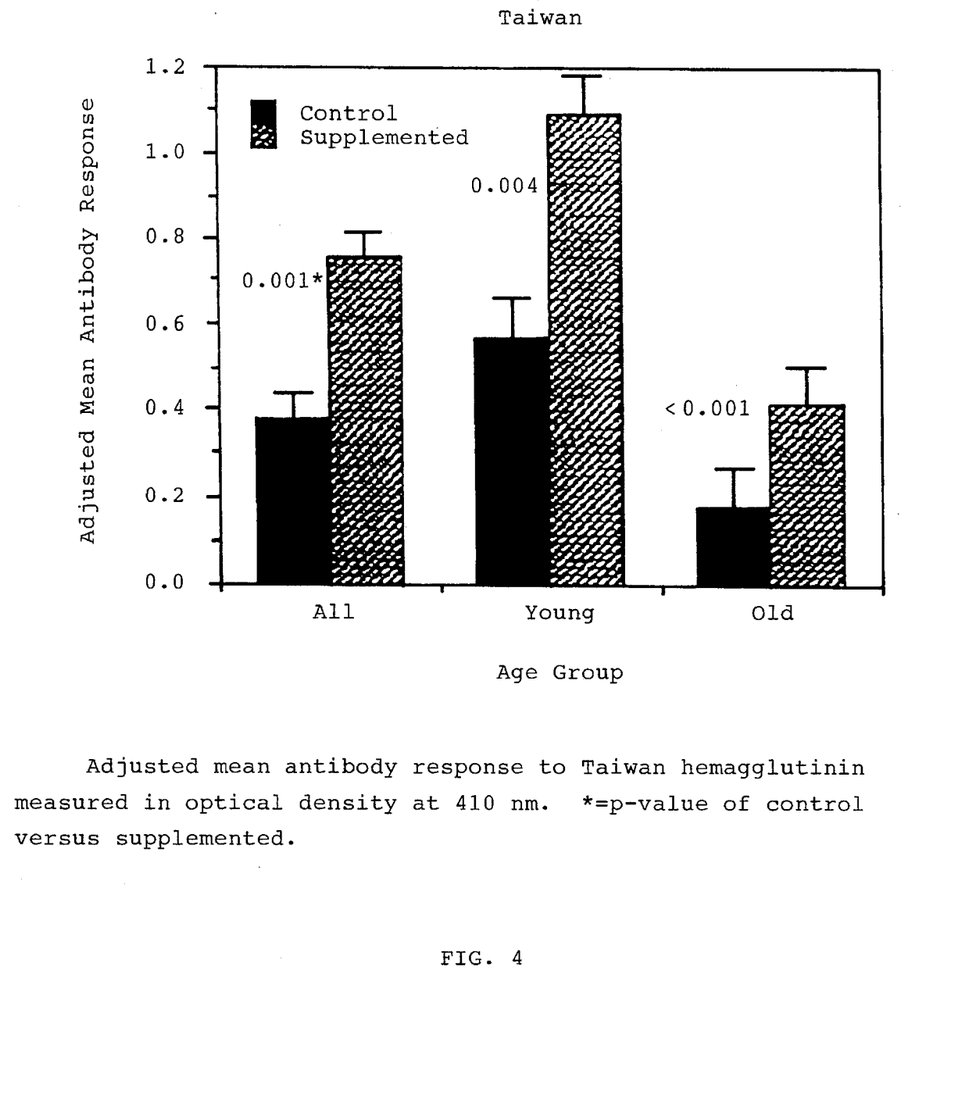

The data in FIGS. 2, 3, and 4 shows the mean optical densities that were obtained from the post-sera samples of the mice for all of the groups as well as a compounding of the optical densities of both the young and old mice for each vaccine.

Figure 5:
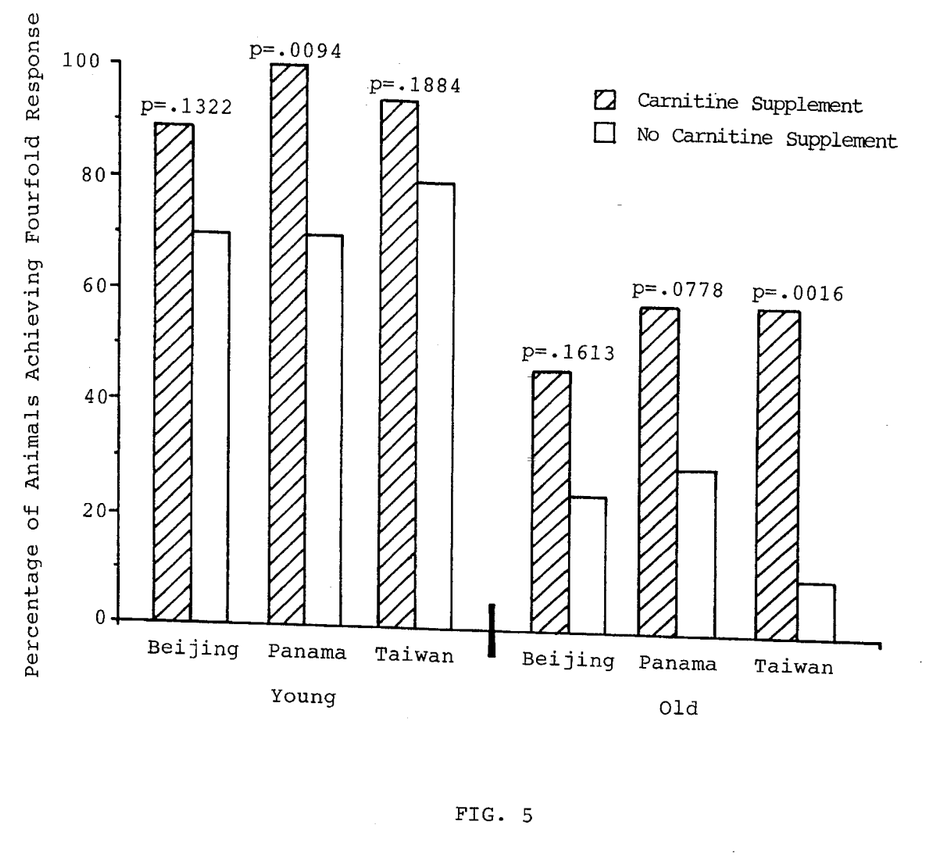
FIG. 5 is a histogram showing the percentage of mice administered either the A/Beijing/H3N2 vaccine, B/Panama/45 vaccine, or A/Taiwan/H1N1 vaccine that achieved a fourfold increase in antibody level three weeks after vaccination.

FIG. 5 is a histogram showing the percentage of the mice in each of the twelve groups that at three weeks post-vaccination had a specific antibody level at least four times higher than in the pre-sera sample ("fourfold response"). As can be seen from this figure, in each pair of groups, a higher percentage of the mice fed the diet supplemented with L-carnitine achieved a fourfold response compared to their paired controls fed standard unsupplemented chow. This apparent ability of L-carnitine to enhance the antibody response of the animals was particularly effective in the old mice given the A/Taiwan/H1N1 vaccine, as already seen in Example 1. In the group of old animals administered the A/Taiwan/H1N1 vaccine, 59% of the mice fed the L-carnitine supplemented diet responded to the vaccine with fourfold higher antibody levels as compared to only 10% of the mice fed unsupplemented chow. In the identically aged mice administered the B/Panama/45 vaccine, 30% of the control versus 59% of the experimental animals achieved a fourfold antibody response. Last, in the aged mice administered the A/Beijing/H3N2 vaccine, 25% of the control versus 47% of the experimental animals had post-sera antibody levels at least four times higher than the levels in the pre-sera samples. Thus, in the older population of animals, treatment with L-carnitine resulted in at least twice the number of animals responding with a fourfold increase in antibody levels. In contrast, in the young population of mice, although they also showed improved antibody responsiveness when treated with L-carnitine, the percent improvement was lower. This suggests that, at least for some antigens, L-carnitine treatment of animals with compromised immune systems in conjunction with vaccine administration can substantially improve antibody response. It further suggests that L-carnitine may also be useful as an adjuvant even under conditions of optimal immune responsiveness.

EXAMPLE 3: Effect of L-carnitine treatment of Balb/c mice on antibody levels attained 4 weeks after administration of the Tetanus Toxoid vaccine.

Thirty Eight young and Thirty Five old mice were vaccinated with 5 µg of the Tetanus Toxoid vaccine. After vaccination the two age groups were divided, as in Example 1, such that 18 of the young mice and 16 of the old mice were fed a diet to which L-carnitine had been supplemented while the rest of the mice were maintained on standard unsupplemented rodent chow. Collection of serum samples, antibody assay, and data analysis was performed as indicated in Example 1 except that the post-vaccination serum sample was obtained 4 weeks after vaccination.

The response of the Tetanus Toxoid was so high already, it wasn't significantly increased by carnitine. This is true also of almost all other effective adjuvants with respect to Tetanus Toxoid antigen production.

Specificity of carnitine adjuvant action is shown by the fact that the immune response is much greater for the Taiwan antigen than Beijing or Panaman and that there is also a difference in response between young and old mice with Beijing (young better P= 0.001) and with Panama (old better P= 0.003).

EXAMPLE 4: Effect of treatment of Balb/c mice with L-carnitine, L-carnitine derivatives, or L-carnitine precursors on antibody levels attained 3 weeks after administration of three influenza vaccines.

Three month old mice were divided into five groups based on dietary supplement added to the Purina 5001 Rodent Chow. The five groups were: no supplement (control), low dose L-carnitine (LCL; 50 mg/kg/day), high dose L-carnitine (LCH; 100 mg/kg/day), low dose Acetyl-L-carnitine (ALCL; molar equivalent of the LCL dose), high dose Acetyl-L-carnitine (ALCH; molar equivalent of the LCH dose), and low dose Gamma-butyrobetaine (GBBL; molar equivalent of the LCL dose). The supplements were added to the chow as described in Example 1. Mice within each diet group were administered 5 µg each of the A/Beijing/H3N2, B/Panama/45, and A/Taiwan/H1N1 vaccines. Collection of serum samples, antibody assay, and data analysis was performed as indicated in Example 1.

TABLE 1

| Antigen | | | |
|---|---|---|---|
| | | A/Beijing/H3N2 | |
| DIET | n | 4000 | 16000 |
| LCL | 5 | 1.47(±0.27) | 0.99(±0.27) |
| LCH | 5 | 1.64(±0.12) | 1.19(±0.12) |
| ALCL | 5 | 0.66(±0.38) | 0.15(±0.38) |
| ALCH | 5 | 0.72(±0.3) | 0.78(±0.3) |
| GBBL | 4 | 1.04(±0.36) | 0.53(±0.36) |
| Control | 9 | 0.4(±0.16) | 0.19(±0.16) |
| | | B/Panama | |
| DIET | n | 4000 | 16000 |
| LCL | 5 | 4.3(±1.84) | 0.91(±1.84) |
| LCH | 5 | 0.97(±0.88) | 0.13(±0.88) |
| ALCL | 5 | 1.01(±0.35) | 0.36(±0.35) |
| ALCH | 5 | 0.93(±0.27) | 0.46(±0.27) |
| GBBL | 4 | 1.59(±0.23) | 0.71(±0.23) |
| Control | 7 | 0.39(±0.2) | 0.05(±0.2) |
| | | A/Taiwan/H1N1 | |
| DIET | n | 4000 | 16000 |
| LCL | 4 | 1.06(±0.32) | 0.49(±0.32) |
| LCH | 5 | 1.94(±0.3) | 1.38(±0.3) |
| ALCL | 5 | 0.75(±0.21) | 0.21(±0.21) |
| ALCH | 5 | 1.68(±0.52) | 0.67(±0.52) |
| GBBL | 3 | 2.39(±0.85) | 1.09(±0.85) |
| Control | 4 | 0.8(±0.28) | 0.52(±0.28) |

The mean optical densities obtained from the post-vaccination serum samples at both 1/4000 and 1/16000 dilutions are tabulated in Table 1 by dietary supplement and influenza vaccine. These data indicate that the best overall antibody response to the vaccines occurred in the animals receiving low dose L-carnitine (LCL) and low dose gamma-butyrobetaine (GBBL). The animals receiving a diet supplemented with low and high dose Acetyl-L-carnitine showed little or no improvement compared to the control or the other treatments. Further, these data indicate LC and GBB stimulate antibody formation, while Acetyl-L-carnitine (ALC) does not. The Cavazza '588 patent (discussed above) refers only to Acetyl-L-carnitine and says L-carnitine had little or no effect. The Cavazza '588 patent describes a totally different phenomena than is discussed here.

We claim:

1. A method for increasing antibody production in response to vaccine administration in an animal, comprising treating said animal with an effective amount of a compound of formula (I):

wherein $R_1$ is hydrogen or hydroxyl.

2. The method of claim 1, wherein said effective amount is an amount effective to increase antibody production to an influenza antigen in said animal.

3. The method of claim 2, wherein said influenza antigen is derived from A/Beijing/H3N2, B/Panama/45 or influenza virus strains A/Taiwan/H1N1.

4. The method of claim 1, wherein said effective amount is a daily dose of about 5 mg/kg to about 500 mg/kg body weight.

5. The method of claim 1, wherein said effective amount is a daily dose of about 10 mg/kg body weight to about 100 mg/kg body weight.

6. The method of claim 4, wherein said daily dose is divided into several separately administered doses.

7. The method of claim 1, wherein said compound is administered orally.

8. A method of claim 1, wherein said compound is administered by injection.

9. A method according to claim 1, wherein said compound is administered contemporaneously with the vaccine.

10. A method for increasing antibody production in response to vaccine administration in a human, comprising treating said human with an effective amount of a compound of formula (I):

wherein $R_1$ is hydrogen or hydroxyl.

11. The method of claim 10, wherein said effective amount is an amount effective to increase antibody production to an influenza antigen in said human.

12. The method of claim 10, wherein said influenza antigen is derived from A/Beijing/H3N2, B/Panama/45 or influenza virus strains A/Taiwan/H1N1.

13. The method of claim 10, wherein said effective amount is a daily dose of about 5 mg/kg to about 500 mg/kg body weight.

14. The method of claim 10, wherein said effective amount is a daily dose of about 10 mg/kg body weight to about 100 mg/kg body weight.

15. A method according to claim 14 wherein said daily dosage is divided into several separately administered dosages.

16. A method according to claim 10 wherein the compound is administered orally.

* * * * *